United States Patent
Kalmanson et al.

(10) Patent No.: US 11,730,889 B2
(45) Date of Patent: Aug. 22, 2023

(54) TRANQUILIZER DART AND DELIVERY SYSTEM FOR SAME

(71) Applicant: Mitchel Kalmanson, Maitland, FL (US)

(72) Inventors: Mitchel Kalmanson, Maitland, FL (US); Kenneth Murray, Gotha, FL (US); Renier Van Den Berg, Haaksbergen (NL)

(73) Assignee: Mitchel Kalmanson, Maitland, FL (US)

( * ) Notice: Subject to any disclaimer, the term of this patent is extended or adjusted under 35 U.S.C. 154(b) by 315 days.

(21) Appl. No.: 17/247,226

(22) Filed: Dec. 4, 2020

(65) Prior Publication Data

US 2021/0299357 A1    Sep. 30, 2021

Related U.S. Application Data

(60) Provisional application No. 63/001,728, filed on Mar. 30, 2020.

(51) Int. Cl.
| | | |
|---|---|---|
| *F41B 11/723* | (2013.01) | |
| *F41B 11/85* | (2013.01) | |
| *A61M 5/20* | (2006.01) | |
| *A01M 27/00* | (2006.01) | |

(52) U.S. Cl.
CPC ......... *A61M 5/2053* (2013.01); *F41B 11/723* (2013.01); *F41B 11/85* (2013.01); *A01M 27/00* (2013.01); *A61M 2205/3331* (2013.01); *A61M 2205/583* (2013.01)

(58) Field of Classification Search
CPC ........ F41B 11/723; F41B 11/85; F41B 11/724
See application file for complete search history.

(56) References Cited

U.S. PATENT DOCUMENTS

| | | | |
|---|---|---|---|
| 3,690,026 A * | 9/1972 | Rose | F41B 11/85 42/105 |
| 6,474,325 B2 * | 11/2002 | Rice | F41A 19/01 124/75 |
| 6,615,814 B1 * | 9/2003 | Rice | F41B 11/723 124/71 |
| 8,640,684 B2 | 2/2014 | Erez et al. | |

(Continued)

OTHER PUBLICATIONS

International Search Report in related application PCT/US2021/070335 dated Jun. 18, 2021; 3 pages.

(Continued)

*Primary Examiner* — Jonathan C Weber
(74) *Attorney, Agent, or Firm* — Widerman Malek, PL; Daniel C. Pierron

(57) ABSTRACT

A dart delivery apparatus including a handle, trigger, barrel, and frame comprising a dart chamber, a pressure control apparatus including a gas source port, an adjustable pressure control apparatus chamber, a gun port configured to attach to the frame, an expansion chamber, an adjustable pressure regulator configured to be actuated by a user to permit pressurized gas to flow from the gas source port, through the pressure control apparatus chamber, and into the gun port and the expansion chamber, and a shot volume modification apparatus configured to change the volume of the expansion chamber into which pressurized gas may expand.

16 Claims, 9 Drawing Sheets

(56) References Cited

U.S. PATENT DOCUMENTS

| | | | |
|---|---|---|---|
| 2002/0017286 A1* | 2/2002 | Rice | F41B 11/62 |
| | | | 124/71 |
| 2006/0011090 A1* | 1/2006 | Vasel | F42B 5/02 |
| | | | 102/512 |
| 2006/0032487 A1 | 2/2006 | Tippmann et al. | |
| 2006/0107939 A1 | 5/2006 | Dobbins | |
| 2010/0154766 A1* | 6/2010 | Skilling | F41B 11/71 |
| | | | 124/71 |
| 2011/0232618 A1 | 9/2011 | Gabrel | |
| 2019/0293383 A1* | 9/2019 | Skilling | F41B 11/723 |

OTHER PUBLICATIONS

Written Opinion in related application PCT/US2021/070335 dated Jun. 18, 2021; 5 pages.

* cited by examiner

TRANQUILIZER DART AND DELIVERY SYSTEM FOR SAME

RELATED APPLICATIONS

This application claims priority under 35 U.S.C. § 119(e) of U.S. Provisional Patent Application Ser. No. 63/001,728 filed on Mar. 30, 2020 and titled Tranquilizer Dart and Delivery System for Same. The content of this application is incorporated herein by reference.

FIELD OF THE INVENTION

The present invention relates to systems and methods for tranquilizer dart delivery, including tranquilizer dart guns.

BACKGROUND OF THE INVENTION

Non-lethal immobilization of human subjects is an important capability in modern security apparatuses. Many modern approaches have focused on administering an electric shock to induce involuntary muscle spasms in the subject, causing them to fall to the ground and lose voluntary control of their body, permitting security personnel to safely approach them and apply physical restraints. However, the necessary voltage to induce such involuntary muscle spasms is significant and can, in certain circumstances, interfere with or exacerbate underlying autonomic or neurologic systems in the subject causing permanent injury or death. Moreover, if another individual who is not the subject is in physical contact with the subject when the electric shock is administered, that person may undesirably also receive a shock.

The use of chemical immobilizers or other biologically active agents in a projectile, such as a tranquilizer dart, is commonly used in the immobilization of non-human animals. While the use of such chemical agents that are administered to a subject is commonly used in hospital settings, their use in a projectile intended for a human subject is uncommon. This is because of many issues associated with delivery methods. Primarily, darts used to deliver chemical immobilizers are designed for use on non-human animals that have thicker hides, reducing the chance of inflicting unintended harm resulting from the impact of the dart on the tissue or skeleton of the target. Generally, the amount of force needed to cause a needle of a dart to penetrate the skin of a human subject is less than for a non-human subject of comparable size. However, that necessary force for a given human subject will vary based on the clothing worn by the human. For example, a linen item of clothing will require little or no additional force, while items like jeans or leather clothing will require significant additional force.

Fine control of the amount of force with which a dart strikes a subject, and necessarily with which the dart is delivered, is necessary to successfully administer the chemical immobilizer without unintentionally injuring the subject. Pneumatic tranquilizer dart delivery systems are known in the art. However, systems that permit the type of fine control necessary for using such systems against human subjects are not known in the art. Accordingly, there is a need in the art for a tranquilizer dart system that enables the user to selectively deliver a desired amount of pneumatic force in the ejection of a dart containing a chemical immobilizer or other immobilizing method.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to systems and apparatuses for the delivery of darts. A first embodiments of the invention is directed to a dart delivery apparatus comprising a handle, a trigger, a barrel, a frame comprising a dart chamber configured to permit a dart assembly to be positioned there within, and a pressure control apparatus comprising a gas source port configured to facilitate attachment of a gas source thereto, thereby permitting fluidic communication between the gas source port and the gas source, an adjustable pressure control apparatus chamber in fluidic communication with the gas source port, a gun port in fluidic communication with the pressure control apparatus chamber and configured to attach to the frame and thereby establish fluidic communication with the dart chamber, an expansion chamber positioned in fluidic communication with the gun port, an adjustable pressure regulator positioned within the pressure control apparatus chamber configured to be actuated by a user to permit pressurized gas to flow from the gas source port, through the pressure control apparatus chamber, and into the gun port and the expansion chamber, and a shot volume modification apparatus positioned partially within the expansion chamber and configured to change the volume of the expansion chamber into which pressurized gas may expand.

In some embodiments, the frame may further comprise a loading aperture configured to permit the dart assembly to pass therethrough and be positioned within the dart chamber, a proximal gasket configured to interface with a proximal section of the dart assembly when the dart assembly is positioned within the dart chamber, and a distal gasket configured to interface with a distal section of the dart assembly when the dart assembly is positioned within the dart chamber.

In some embodiments, the frame may further comprises a gas conduit in fluidic communication with a distal end of the dart chamber, a gas entry chamber in fluidic communication with the gas conduit, a trigger valve configured to be actuated by the trigger to permit fluidic flow from the gas entry chamber to the gas conduit, and a gas entry port in fluidic communication with the gas entry chamber and configured to facilitate attachment of the pressure control apparatus thereto.

In some embodiments, the pressure control apparatus may further comprise a pressure relief apparatus positioned fluidic communication with the gun port and configured to be actuated to permit pressurized gas to flow from the gun port to the environment, thereby de-pressurizing the gun port and the expansion chamber. In some embodiments, the pressure control apparatus may further comprise a pressure display positioned and configured to measure a pressure of gas within the gun port and expansion chamber and display the measured pressure.

In some embodiments, the adjustable pressure regulator may comprise a body member defining an internal cavity and configured to establish a fluidic seal with the adjustable pressure control apparatus chamber such that gas may not flow around the body member from a proximal portion of the adjustable pressure control apparatus chamber to a distal portion thereof, a translating member positioned within the internal cavity of the body member and comprising a translating member conduit, a biasing member configured to bias the translating member in a first position that prevents gas from flowing through the adjustable pressure regulator, a distal plug member comprising a distal plug conduit, and an actuation member attached to the translating member and configured to be actuated by a user to translate the translating member to a second position that permits gas to flow through from a proximal portion of the adjustable pressure control apparatus chamber though the translating member conduit, the distal portion of the adjustable pressure control apparatus chamber, and the distal plug conduit to the gun port.

In some embodiments, the shot volume modification apparatus may comprise an attachment member configured to attach to the expansion chamber and be positioned partially there within, a cap member attached to a distal end of the attachment member, positioned partially within the expansion chamber and configured to translate longitudinally along the attachment member, and a gasket configured to establish a fluidic seal between the cap member and the expansion chamber such that gas does not flow out of the expansion chamber past the cap member. The longitudinal translation of the cap member may change the volume of the expansion chamber.

Another embodiment of the invention is directed to a dart delivery apparatus comprising a handle, a trigger, a barrel, a frame comprising a dart chamber configured to permit a dart assembly to be positioned there within, and a pressure control apparatus comprising a gas source port configured to facilitate attachment of a gas source thereto, thereby permitting fluidic communication between the gas source port and the gas source, an adjustable pressure control apparatus chamber in fluidic communication with the gas source port, a gun port in fluidic communication with the pressure control apparatus chamber and configured to attach to the frame and thereby establish fluidic communication with the dart chamber, an expansion chamber positioned in fluidic communication with the gun port, and an adjustable pressure regulator positioned within the pressure control apparatus chamber configured to be actuated by a user to permit pressurized gas to flow from the gas source port, through the pressure control apparatus chamber, and into the gun port and the expansion chamber. The adjustable pressure regulator may comprise a body member defining an internal cavity and configured to establish a fluidic seal with the adjustable pressure control apparatus chamber such that gas may not flow around the body member from a proximal portion of the adjustable pressure control apparatus chamber to a distal portion thereof, a translating member positioned within the internal cavity of the body member and comprising a translating member conduit, a biasing member configured to bias the translating member in a first position that prevents gas from flowing through the adjustable pressure regulator, a distal plug member comprising a distal plug conduit, and an actuation member attached to the translating member and configured to be actuated by a user to translate the translating member to a second position that permits gas to flow through from a proximal portion of the adjustable pressure control apparatus chamber though the translating member conduit, the distal portion of the adjustable pressure control apparatus chamber, and the distal plug conduit to the gun port, and a shot volume modification apparatus positioned partially within the expansion chamber and configured to change the volume of the expansion chamber into which pressurized gas may expand, the shot volume modification apparatus comprising an attachment member configured to attach to the expansion chamber and be positioned partially there within, a cap member attached to a distal end of the attachment member, positioned partially within the expansion chamber and configured to translate longitudinally along the attachment member, and a gasket configured to establish a fluidic seal between the cap member and the expansion chamber such that gas does not flow out of the expansion chamber past the cap member. Longitudinal translation of the cap member may change the volume of the expansion chamber.

BRIEF DESCRIPTION OF THE DRAWINGS

Some embodiments of the present invention are illustrated as an example and are not limited by the figures of the accompanying drawings, in which like references may indicate similar elements.

DETAILED DESCRIPTION OF THE INVENTION

Figure 1:
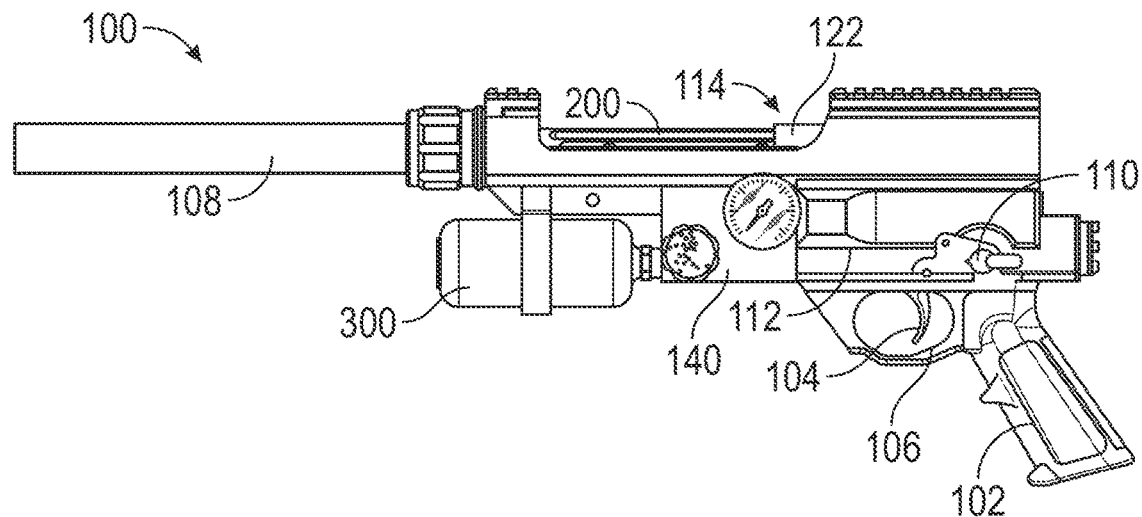
FIG. 1 is a side view of a dart delivery system in the form of a gun according to an embodiment of the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a dart and a delivery system for the same. Specifically, FIGS. 1-7 show a gun 100, a dart 200, a pressure control apparatus 140, and a gas source 300 according to an embodiment of the invention. The gun 100 may be configured to utilize pneumatic pressure to eject the dart 200 in the direction of a target.

The gun 100 may comprise structures typical of similar devices, including a handle 102, a trigger 104, a trigger guard 106, a barrel 108, a frame 112, and a safety switch 110 configured to include to positions, one of which permits the trigger 104 to be pulled and the dart 200 ejected from the gun 100, and the other that prevents the trigger 104 from being pulled, thereby preventing unintentional firing.

The frame 112 may comprise a loading aperture 114 configured to permit the dart 200 to pass therethrough and be loaded into the gun 100. The frame 112 may further comprise a dart chamber 116 into which the dart 200 may be positioned. The frame 112 may further comprise a proximal gasket 118 and a distal gasket 120 positioned within the dart chamber 116 to facilitate the loading of the dart 200. More specifically, each of the proximal and distal gaskets 118, 120 may interface with the dart 200 when the dart 200 is positioned within the dart chamber 116. Such interfacing may at least one of exert a frictional force on the dart 200 to require an increase force to dislodge the dart 200 therefrom, thereby making the unintentional dislodging of the dart 200 less likely, and establish an at least partial, and in some embodiments complete, fluidic seal between the gasket and the dart 200 to facilitate the ejection of the dart 200 from the gun 100, as will be described in greater detail hereinbelow. In some embodiments, the proximal and distal gaskets 118, 120 may be in the form of an o-ring.

Figure 3:
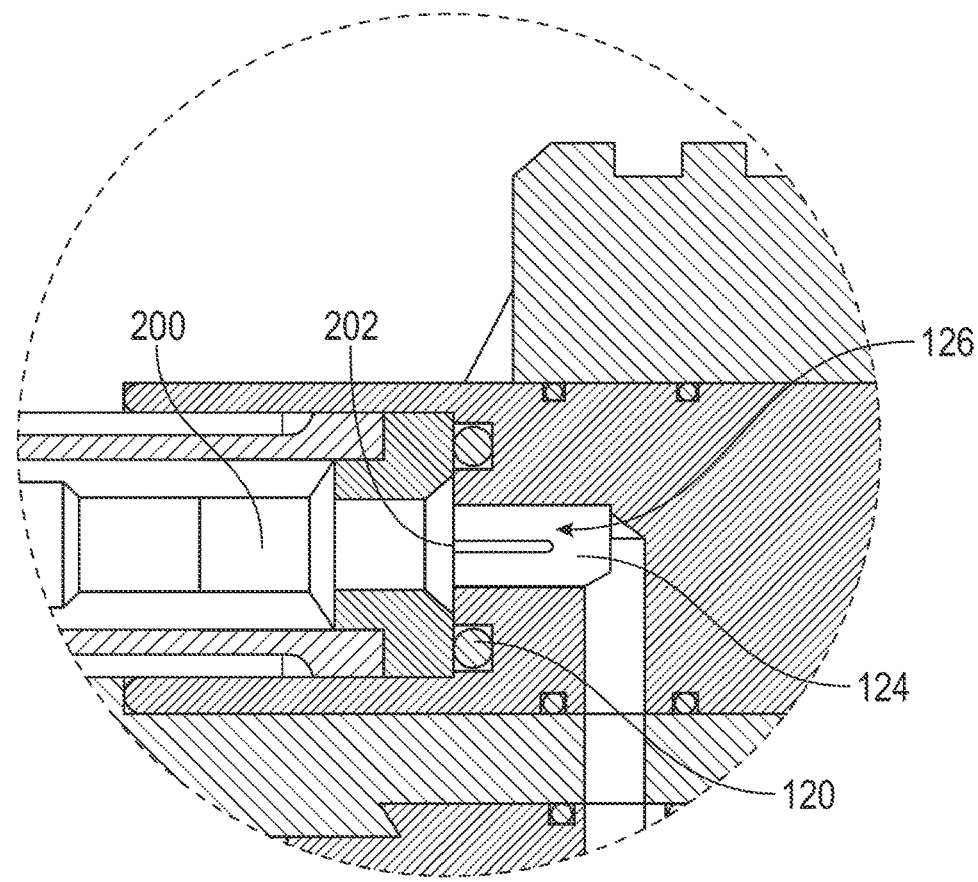
FIG. 3 is a detailed sectional view of a portion of the gun of FIG. 1
Figure 4:
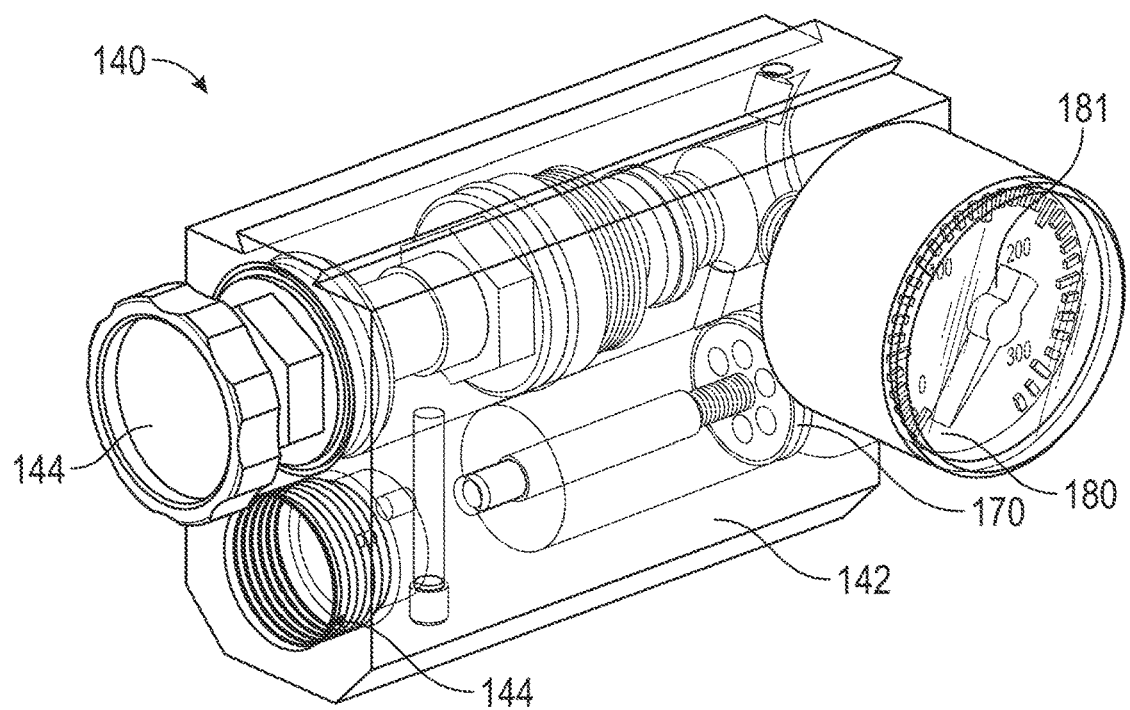
FIG. 4 is a perspective view of a pressure control apparatus of the gun of FIG. 1 with a housing thereof being partially transparent.
Figure 14:
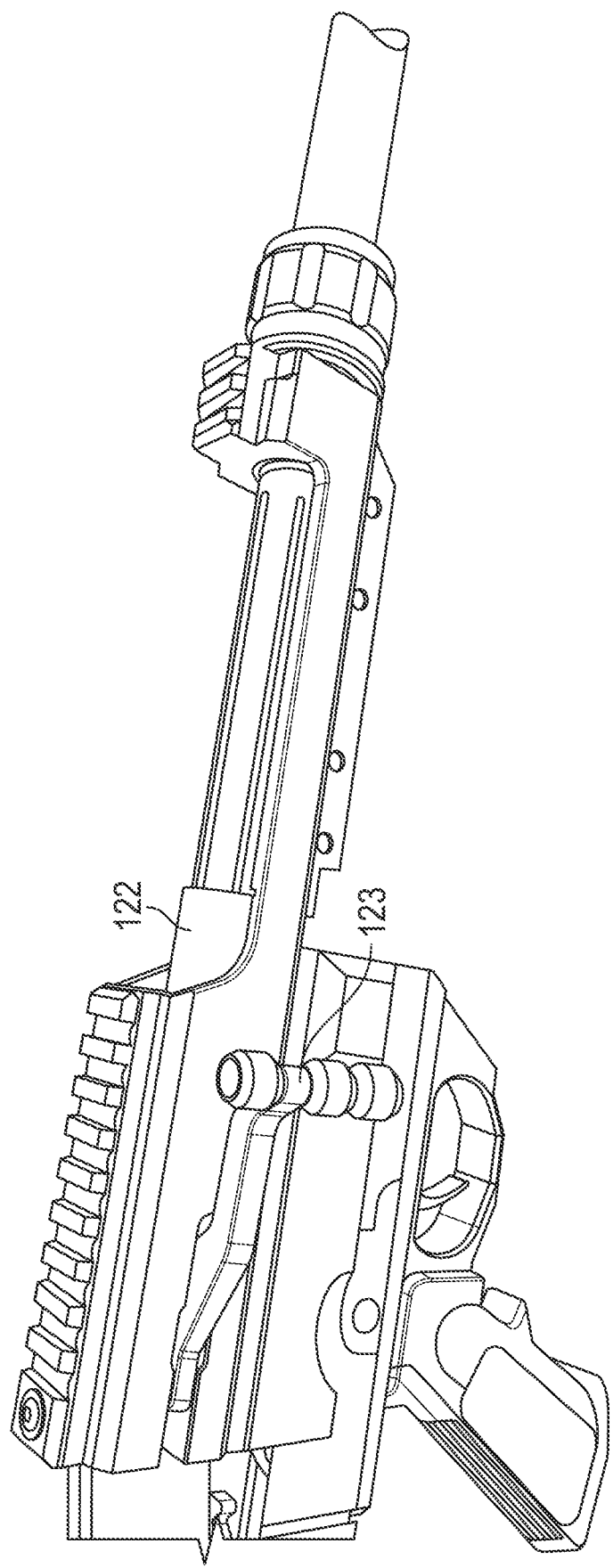
FIG. 14 is an opposite side perspective image of the dart delivery system of FIG. 1.

The gun 100 may further comprise a bolt 122. The bolt 122 may be laterally actuatable to facilitate the loading and unloading of the dart 200 as well as facilitate pressure-sealing the dart 200 and the distal gasket 120 to enable ejection of the dart 200 from the gun 100. In some embodiments, the distal gasket 120 may be carried by the bolt 122. In a first position, the bolt 122 may be positioned in a distal position, such that the bolt 122 is positioned largely out of the loading aperture 114 and permits the dart 200 to be positioned within the dart chamber 116. Once the dart 200 is positioned within the dart chamber 116, the user may laterally translate the bolt 122 in a proximal direction to a second position. Such lateral translation in a proximal direction may cause the interfacing between the dart 200 and the distal gasket 120. Additionally, where the dart 200 is positioned in a relatively distal position such that it does not interface with the proximal gasket 118, the interface between the distal gasket 120 and the dart 200 in conjunction with the proximal translation of the bolt 122 may cause the dart 200 to similarly translate in a laterally proximal direction, such that the dart may interface with the proximal gasket 118. Specifically, and as best seen in FIG. 3, the proximal gasket 118 may interface with a proximal surface of the dart 200, thereby establishing a fluidic seal with the dart 200. The bolt 122 may be actuate by any method or structure as is known in the art. As seen in FIG. 14, the bolt 122 may be actuated by a lever 123 operable by the user.

Figure 2:
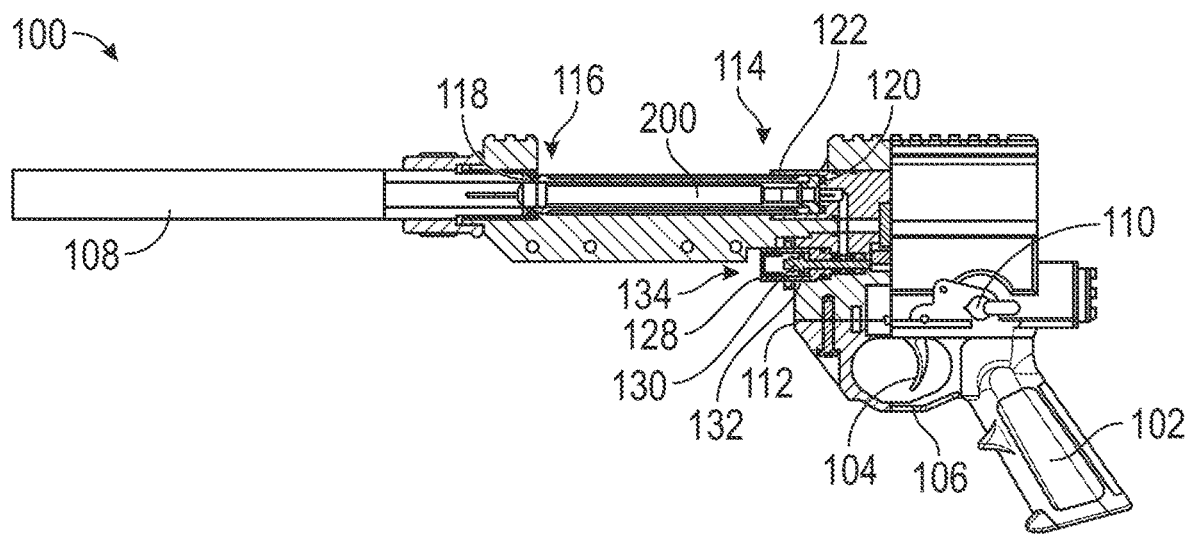
FIG. 2 is a side, partial sectional view of the gun of FIG. 1.

As best seen in FIG. 2, the proximal gasket 118 may generally surround an outer surface of the dart 200 and interface there with, such that lateral translation of the dart in a proximal direction requires overcoming the friction established between the dart 200 and the proximal gasket 118. This may advantageously prevent the dart 200 from unintentionally translating proximally out of the dart chamber 116, through the barrel 108, and out of the gun 100, particularly when the gun 100 is held by the user such that the barrel 108 is pointed downwards.

To further prevent the unintentional ejection or removal of the dart 200 from the gun 100, the bolt 122 may be configured such that, when the dart 200 is positioned in the dart chamber 116 and the bolt 122 is translated in a laterally proximal direction to the second position, the bolt 122 may at least partially overly a section of the dart 200. Such overlaying of the dart 200 by the bolt 122 may prevent the dart 200 from unintentionally exiting the gun through the loading aperture 114, particularly when the gun 100 is being held vertically or is inverted.

The frame 112 may comprise a gas conduit 124. The gas conduit 124 may be configured to be in fluidic communication with a distal end of the dart chamber 116 at a distal aperture 126 thereof. The distal gasket 120 may be positioned to generally circumscribe one or both of the gas conduit 124 and the distal aperture 126. When the bolt 122 is in the second position such that it is translated proximally, the gas conduit 124 may be in fluidic communication with a distal surface 202 of the dart 200 via the distal aperture 126, such that an increase in gaseous pressure within the gas conduit 124 may exert a force upon the distal surface 202 of the dart 200, causing the dart to translate proximally past the proximal gasket 118, out of the dart chamber 116, through the barrel 108, and out of the gun 100 in a trajectory along a longitudinal axis of the barrel 108.

The gun 100 may further comprise a gas entry chamber 128. The gas entry chamber 128 may be positioned in fluidic communication with the gas conduit 124 such that gas may flow through the gas entry chamber 128 into the gas conduit 124. The gun 100 may further comprise a trigger valve 130 The trigger valve 130 may be configured to interface and form a fluidic seal with a portion of the gas entry chamber 128 to prevent gas from flowing into the gas conduit 124. In the present embodiment, the trigger valve 130 may interface with a gas chamber exit aperture 132. The trigger valve 130 may be biased to maintain the seal prior to actuation. Such bias may be accomplished by exerting a force upon the trigger valve 130, such force being exerted by a mechanical source, such as a spring, or a magnetic force, such as magnetic attracting between the trigger valve 130 and a portion of the gas entry chamber 128 adjacent the gas chamber exit aperture 132. In some embodiments, the gas entry chamber 128 may comprise a gas exit gasket 133 positioned to interface with each of the wall of the gas entry chamber 128 and the trigger valve 130 to facilitate establishing a fluidic seal there between. The trigger valve 130 may be actuated by the trigger 104, namely, when a user actuates the trigger 104 by pulling it, the trigger valve 130 may break the fluidic seal by translating away from the gas chamber exit aperture 132, thereby permitting gas to flow past the trigger valve 130, through the gas chamber exit aperture 132, and into the gas conduit 124.

The gas entry chamber 128 may further comprise a gas entry port 134. The gas entry port 134 may be configured to attach to the pressure control apparatus 140 and establish fluidic communication between the gas entry chamber 128 and the pressure control apparatus 140. In the present embodiment the gas entry port 134 comprises threading configured to cooperate with threading of a structure of the pressure control apparatus 140 to establish a fluidic communication there between while also preventing fluidic leakage from such fluidic communication. All connection means and methods as are known in the art are contemplated and included within the scope of the invention. Gas pressure that is established by the user in the pressure control apparatus 140 may similarly be established in the gas entry chamber 128 by fluidic communication between the gas entry port 134 and the pressure control apparatus 140. When the trigger valve 130 is actuated, that gas pressure may flow through gas chamber exit aperture 132, through the gas conduit 124, through the distal aperture 126 and exert a force on the dart 200, thereby ejecting the dart 200 through the barrel 108 and out of the gun 100.

The pressure control apparatus 140 may be configured to permit a user to control the pressurization of gas received from the gas source 300 and delivery of gas to the gas entry chamber 128. The pressure control apparatus 140 may comprise a housing 142, an adjustable pressure regulator 150, a pressure display 180, and a shot volume modification apparatus 170. The housing 142 may define a gas source port 144 configured to facilitate attachment to the gas source 300. Such attachment may establish fluidic communication between the pressure control apparatus 140 and the gas source 300. Such fluidic communication may permit gas to flow from the gas source 300 to the pressure control apparatus 140.

The housing 142 may further comprise a gas source conduit 143 and a pressure control apparatus chamber 145. The gas source conduit 143 may be positioned in fluidic communication with the gas source port 144 and the pressure control apparatus chamber 145, such that gas may exit the gas source 300, pass through the gas source port 144, through the gas source conduit 143, and into the pressure control apparatus chamber 145.

The housing 142 may further comprise a gun port 146, an expansion chamber conduit 147, and an expansion chamber 148. The gun port 146 may be positioned in fluidic communication with the pressure control apparatus chamber 145 and the expansion chamber conduit 147, and the expansion chamber conduit 147 may further be in fluidic communication with the expansion chamber 148. Gas may flow from the pressure control apparatus chamber 145 to the gun port 146, then through the expansion chamber conduit 147 to the expansion chamber 148.

The gun port 146 may be configured to attach to the gun 100 and establish fluidic communication there with, such that gas may flow through the gun port 146 to the gun 100. Specifically, the gun port 146 may be configured to connect with the gas entry port 134 of the gun 100 to facilitate gas transfer from the gun port 146 to the gas entry port 134. In the present embodiment, the gun port 146 comprises threads configured to cooperate with the threads of the gas entry port 134 to removably attach the pressure control apparatus 140 to the gun 100 and prevent the leakage of gas into the environment.

The adjustable pressure regulator 150 may be positioned within the pressure control apparatus chamber 145. The adjustable pressure regulator 150 comprises an actuation member 151, a body member 152 defining an internal cavity, a translating member 153 positioned within the internal cavity of the body member 152 and comprising a translating member conduit 154, a biasing member 155, and a distal plug member 156 comprising a distal plug conduit 157. The body member 152 may comprise a proximal gasket 164 positioned to establish a fluidic seal with the adjustable pressure control apparatus chamber 145 such that gas may not flow around the body member 152 from a proximal portion of the chamber 145 to a distal portion thereof. Furthermore, the body member 152 may be configured to removably attach to the chamber 145, for instance, by comprising threads that cooperate with threads of the chamber 145.

The adjustable pressure regulator 150 may be configured to selectively permit gas to pass from the pressure control apparatus chamber 145 to the gun port 146. The biasing member 155 may be any device or structure capable of biasing the translating member 153 in a first position that prevents gas from flowing through the adjustable pressure regulator 150 to the gun port 146. In the present embodiment the biasing member 155 is a spring. Gas may be prevented from flowing through the translating member 153 by the biasing member 155 exerting a force on the translating member 153 in a distal direction such that a downstream end of the translating member conduit 154 abuts and interfaces with a structure of the distal plug member 156, thereby establishing a fluidic seal or fluidic restriction, to prevent the flow of gas out the downstream end of the translating member conduit 154. Further, the translating member 153 may comprise one or more gaskets 159 positioned to prevent the flow of gas around the translating member 153 in the internal cavity. Specifically, the gaskets 159 may interface with each of an outer surface of the translating member 153 and an inner surface of the body member 152, establishing a fluidic seal.

The adjustable pressure regulator 150 may further comprise a proximal attachment member 160. The proximal attachment member 160 may be configured to attach to the housing 142, specifically in an adjustable pressure regulator aperture 141 of the housing 142, thereby attaching the adjustable pressure regulator 150 to the housing 142. The proximal attachment member 160 may be configured to establish a fluidic seal with the housing 142 to prevent the flow of fluid through the adjustable pressure regulator aperture 141. Specifically, the proximal attachment member 160 may comprise one or more gaskets 161 to establish a fluidic seal between the proximal attachment member 160 and the pressure control apparatus chamber 145.

The proximal attachment member 160 may further be configured to attach to the body member 152. The proximal attachment member 160 may comprise an aperture 162 through which the body member 152 may be positioned. Additionally, the proximal attachment member 160 may be configured to include a structure configured to facilitate attachment of the body member 152 thereto. In the present embodiment, the proximal attachment member 160 comprises threads configured to cooperate with threads of the body member 152 to establish attachment there between. Such attachment may also establish a fluidic seal between the proximal attachment member 160 and the body member 152. In the present embodiment, a gasket 163 may be positioned between the body member 152 and the proximal attachment member 160, interfacing with flange members thereof, such that, when the body member 152 screws onto the proximal attachment member 160, a fluidic seal is established therebetween.

Figure 5:
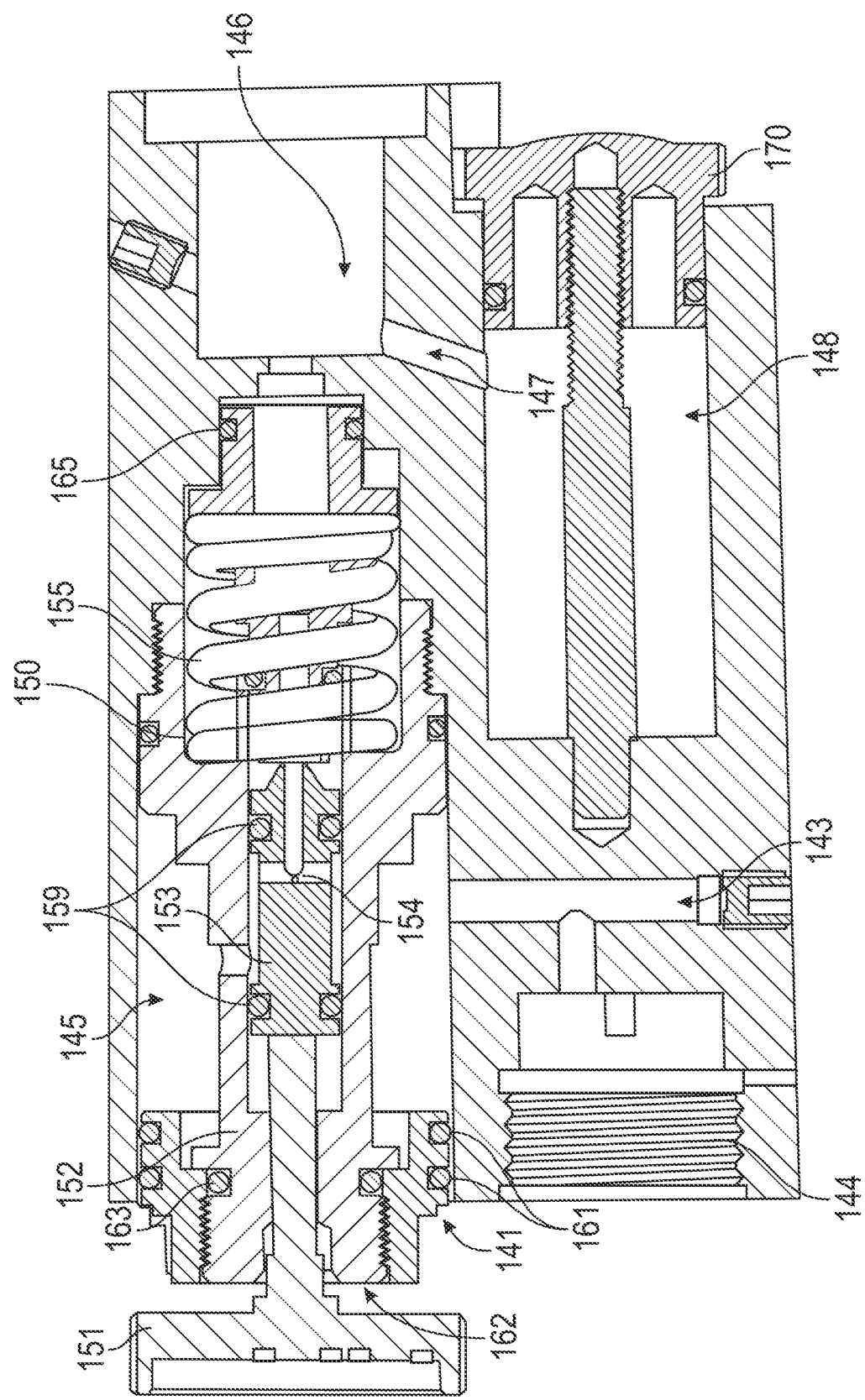
FIG. 5 is a side sectional view of the pressure control apparatus of FIG. 4
Figure 6:
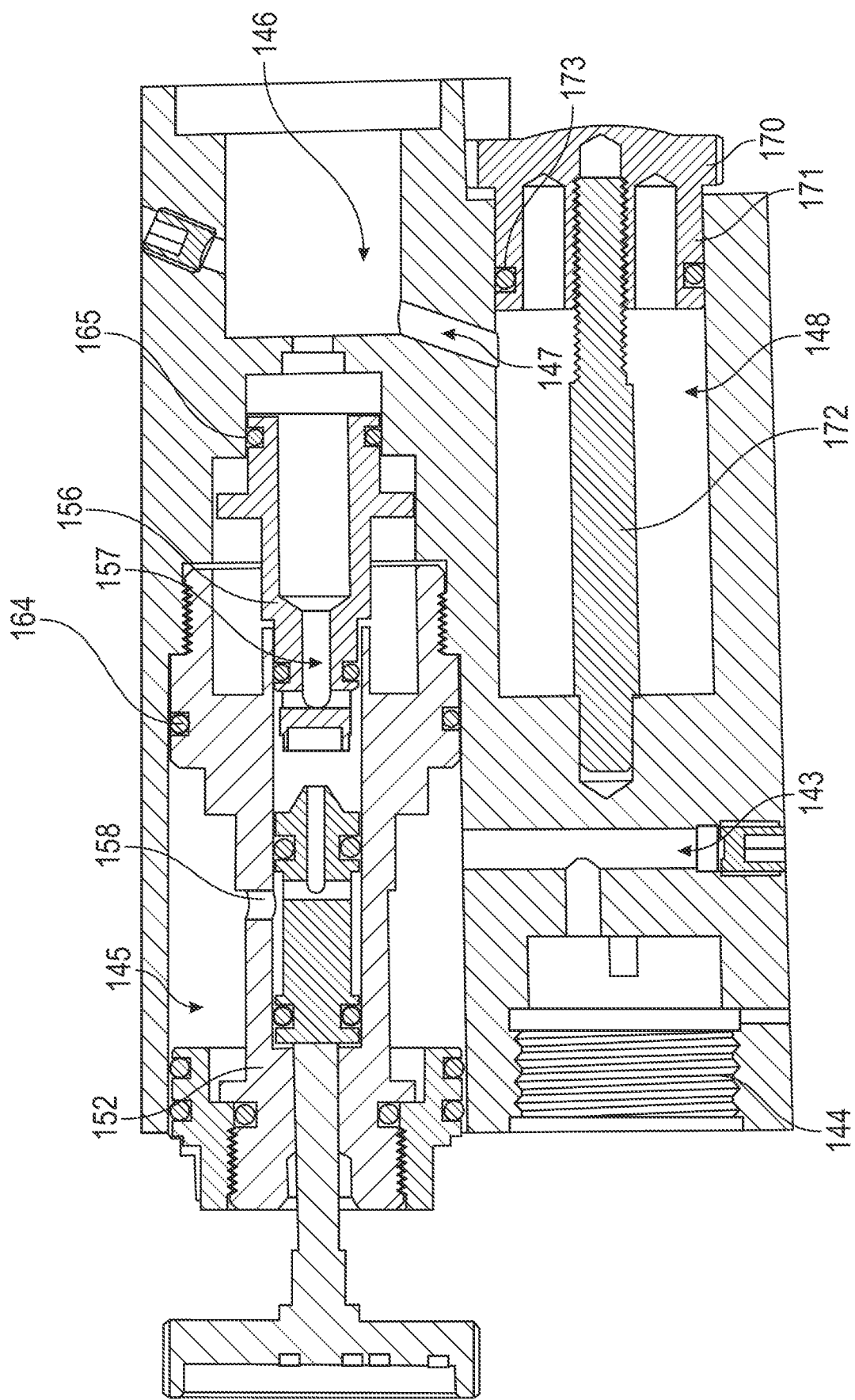
FIG. 6 is a side sectional view of the pressure control apparatus of FIG. 4 in a position configured to permit gas to flow.

The actuation member 151 may be attached to the translating member 153 and operable to translate longitudinally. FIG. 5 depicts the actuation member 151 when it is in the first position, when it is translated longitudinally distal as far as possible. This results in the translating member 153 being positioned in a longitudinally distal position corresponding to the first position. FIG. 6 depicts the actuation member 151 having been translated longitudinally proximal into a second position. In such a position the translating member 153 is also translated to a longitudinally proximal position such that the translating member conduit 154 is positioned in fluidic communication with an inlet aperture 158 of the body member 152, permitting gas in the pressure control apparatus chamber 145 to pass through the inlet aperture 158 and through the translating member conduit 154. The distal plug member 156 may be configured to not translate, i.e. remain stationary, when the translating member 153 translates, thus removing the seal there between. This may permit gas may further flow through a void between the translating member 153 and the distal plug member 156, and further through the distal plug conduit 157 into the gun port 146.

Additionally, the distal plug member 156 may comprise a distal plug distal gasket member 165 configured to interface with the chamber 145, thereby establishing a fluidic seal with a distal portion of the chamber 145 to prevent the flow of gas around the distal plug member 156 to the gun port 146.

As mentioned hereinabove, gas that flows into the gun port 146 may flow through the expansion chamber conduit 147 into the expansion chamber 148. The volume of the expansion chamber 148 may be modified by the shot volume modification apparatus 170. The shot volume modification apparatus 170 may comprise a cap member 171, an attachment member 172, and a gasket 173. The attachment member 172 may be configured to attach to the expansion chamber 148 and be positioned partially there within. Furthermore, a distal end of the attachment member 172 may be configured to attach to the cap member 171. In the present embodiment, the distal end of the attachment member 172 comprises threading configured to cooperate with threading of the cap member 171. The gasket 173 may be positioned to establish a fluidic seal between the cap member 171 and the expansion chamber 148 to prevent the flow of gas out of the expansion chamber 148. Specifically, the gasket 173 may be positioned on a proximal portion of the cap member 171.

The cap member 171 may be positioned at least partially within the expansion chamber 148 and be attached to the attachment member 172. Furthermore, the attachment between the cap member 171 and the attachment member 172 may permit the cap member 171 to translate longitudinally in proximal and distal directions. As the cap member 171 translates proximally, the portion of the cap member 171 positioned within the expansion chamber 148 will increase, thereby occupying more of the volume of the expansion chamber 148. This has the effect of reducing the available volume in the expansion chamber 148, thereby reducing the amount of gas that may occupy the expansion chamber 148 at a given pressure. Similarly, as the cap member 171 translates distally, the portion of the cap member 171 positioned within the expansion chamber 148 will decrease, thereby increase the amount of gas that may occupy the expansion chamber 148 at a given pressure. Such translation may be accomplished by rotating the cap member 171, such that the interaction of the threads thereof with the threads of the attachment member 172 may cause the lateral movement of the cap member 171. Furthermore, the gasket 173 may be configured to permit such lateral translation while maintaining a fluidic seal.

The pressure display 180 may be positioned in fluidic communication with the gun port 146. The pressure display may be operable to measure the pressure of gas within the gun port 146 and the expansion chamber 148, owing to the fluidic communication between the gas port and the expansion chamber 148 via the expansion chamber conduit 147. The pressure display 180 may include a display apparatus 181 operable to display the pressure of gas within the gun port 146. Any display apparatus as is known in the art may be used. In the present embodiment, an analog dial display is used. The user may actuate the adjustable pressure regulator 150 to permit gas to flow into the gun port 146 and the expansion chamber 148 until a desired pressure is displayed on the pressure display 180, at which point the user may discontinue actuation of the adjustable pressure regulator 150 and the pressure may remain until the trigger 104 is actuated by the user, discharging the pressure through the gun 100 and ejecting the dart 200 as described herein above.

Figure 7:
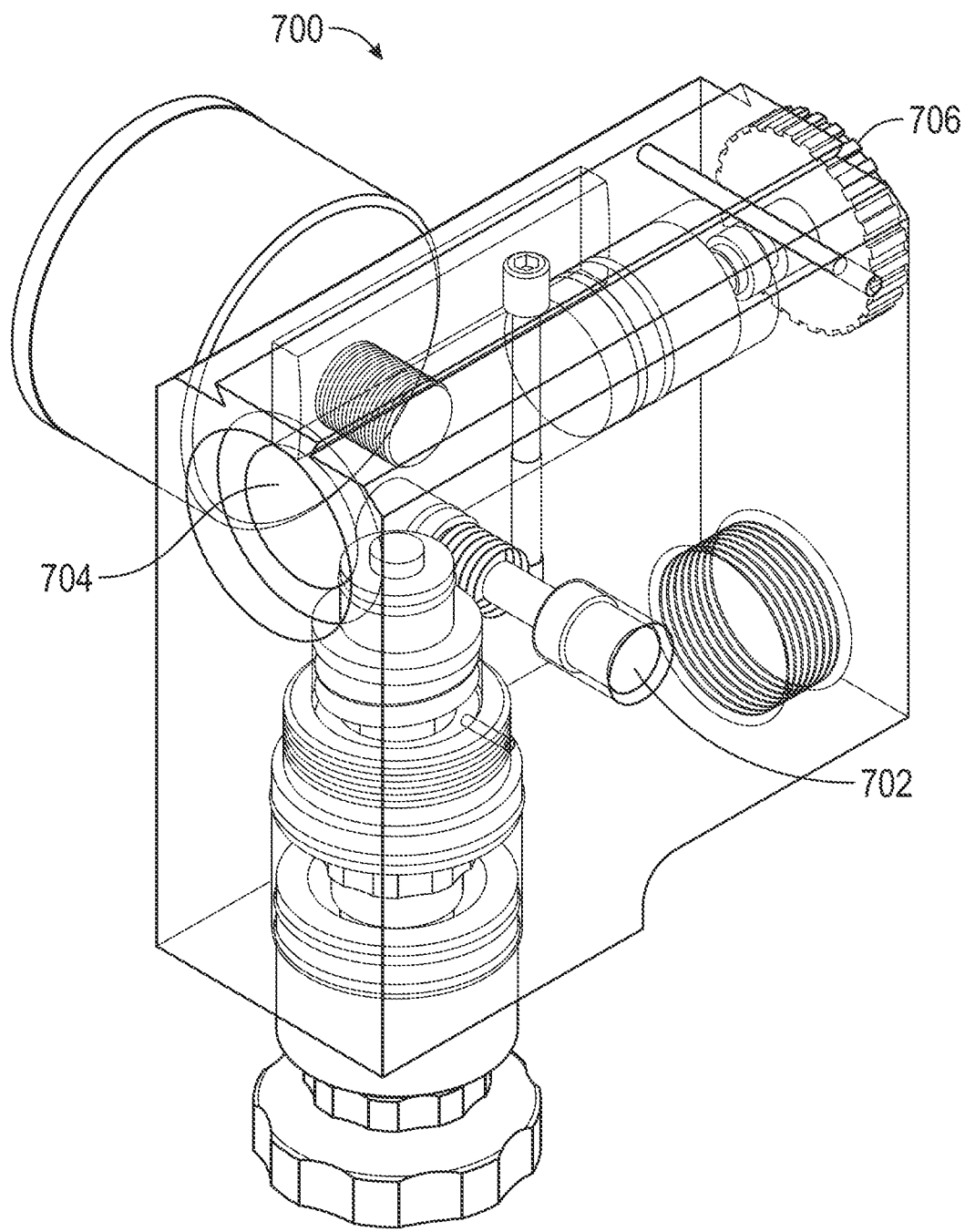
FIG. 7 is a pressure control apparatus according to another embodiment of the invention.
Figure 8:
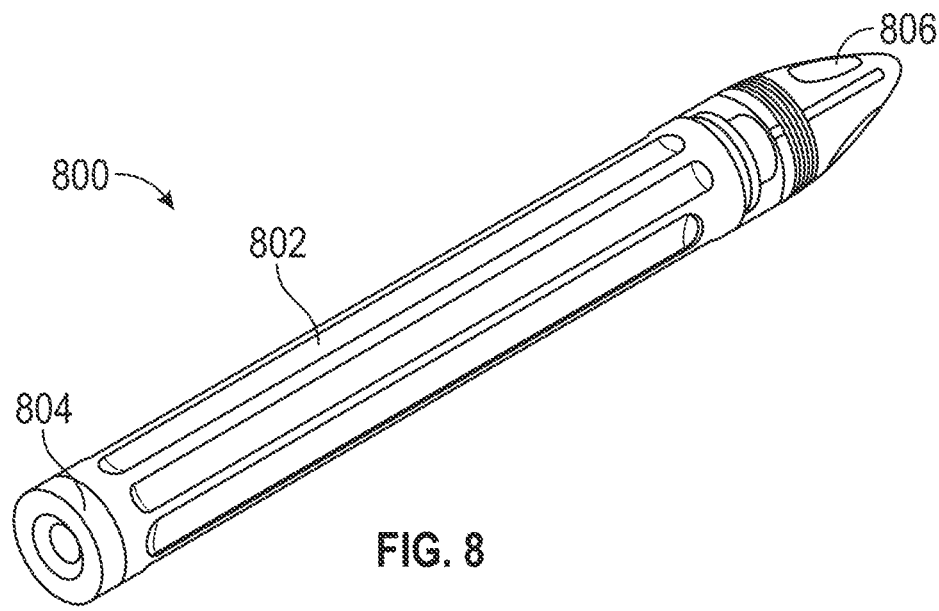
FIG. 8 is a perspective view of a dart according to an embodiment of the invention.
Figure 9:
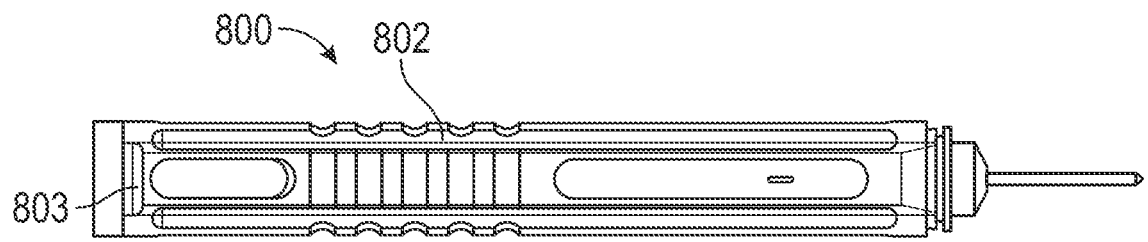
FIG. 9 is a side view of the dart of FIG. 8 with a cap thereof removed.
Figure 10:
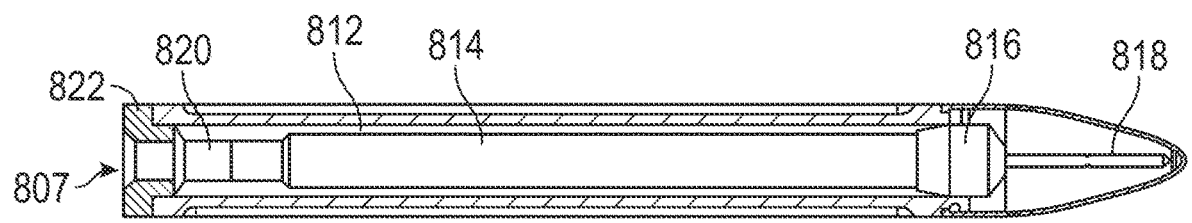
FIG. 10 is a sectional view of the dart of FIG. 8.
Figure 11:
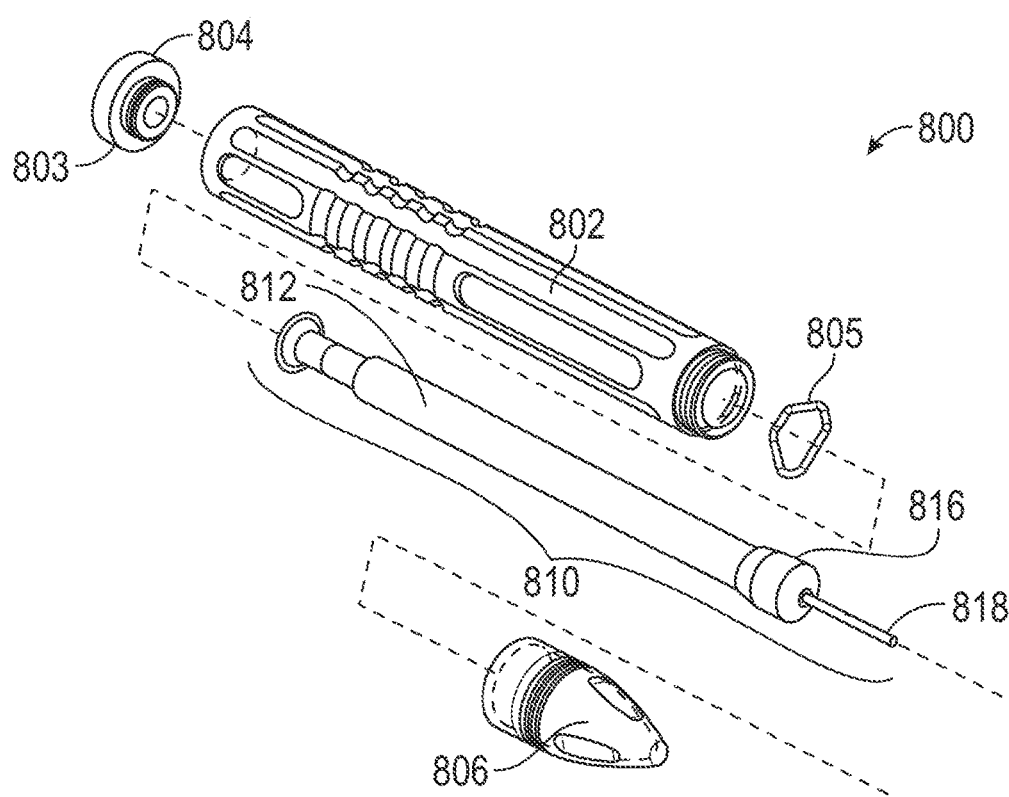
FIG. 11 is an exploded perspective view of the dart of FIG. 8.

FIG. 7 presents an alternative adjustable pressure apparatus 700 according to another embodiment of the invention. The adjustable pressure apparatus 700 may further comprise a pressure relief apparatus 702. The pressure relief apparatus 702 may be positioned in fluidic communication with a gun port 704 of the adjustable pressure apparatus 700. Actuation of the pressure relief apparatus 702 may cause gas in the gun port 704 to flow through the pressure relief apparatus 702, thereby relieving any pressurized gas within the gun port 704. Furthermore, the present embodiment does not include an expansion chamber, and the shot volume modification apparatus 706 is positioned within the gun port 704.

Referring now to FIGS. 8-11, a dart assembly 800 according to an embodiment of the invention is presented. The dart assembly 800 may comprise an outer housing 802, a distal cap member 804, and a proximal cap member 806. The proximal cap member 806 may be configured to be removably attached to a proximal end of the outer housing 802. Any structure or method of removable attachment as is known in the art is contemplated and included within the scope of the invention, include threads, magnets, interference fits, and the like. In the present embodiment, the proximal cap member 806 comprises threads that cooperate with threads on the proximal end of the outer housing 802. Furthermore, a gasket 805 may be positioned intermediate the proximal cap member 806 and the outer housing 802 to facilitate establishing a fluidic seal there between when the proximal cap member 806 is attached to the outer housing 802.

The distal cap member 804 may be attached to a distal end of the outer housing 802. Any method or structure of attachment as is known in the art is contemplated and included within the scope of the invention, as discussed above. In the present embodiment, and interference fit may attach the distal cap member 804 to the outer housing 802. The distal cap member 804 may comprise an extended section 803 configured to extend inward into the interior of the outer housing 802 when attached thereto. The extended section 803 may interface with a distal section of a dart 810 to limit or prevent movement of the dart 810 relative to the outer housing 802. The extended section 803 may define an aperture 807 that positions the interior of the outer housing 802 with the area immediately distal the distal cap member 804. Furthermore, a gasket 801 may be positioned on the extended section 803 to facilitate establishing a fluidic seal between the distal cap member 804 and the outer housing 802 the only fluidic communication into the interior of the outer housing 802 at the distal end thereof is through the aperture 807.

The dart assembly 800 may further comprise a dart 810 comprising a body section 812 defining an internal cavity 814, a needle cap member 816 positioned on a proximal end of the body section 812, a needle 818 extending proximally and attached to the needle cap member 816, and in fluidic communication with the internal cavity 814. The dart 810 may further comprise a distal section 820 including a distal interfacing section 822 configured to interface with the extended section 803 of the distal cap member 804. Such interfacing may place the distal interfacing section 822 in fluidic communication with the area immediately distal the distal cap member 804 via the aperture 807. Accordingly, where there is a gas pressure increase in the area immediately distal the distal cap member 804, such pressure increase may exert a force on the distal interfacing section 822, and accordingly the entire dart 810, pushing the dart 810 in a proximal direction relative to the outer housing 802.

The dart 810 may be contained within the outer housing 802 prior to loading into a dart delivery system, such as the gun 100 of FIG. 1. To load the dart 810 into the dart delivery system, the proximal cap member 806 may be removed and the remaining parts of the dart assembly 800 may positioned within a dart chamber of a dart delivery system, such as the dart chamber as described herein above. For example, when there is a gas pressure increase in the gas conduit 124 described herein above, such a gas pressure increase may cause the dart 810 to be pushed laterally proximal, thereby ejecting the dart 810 from the outer housing 802 and further from the dart delivery system.

Figure 12:
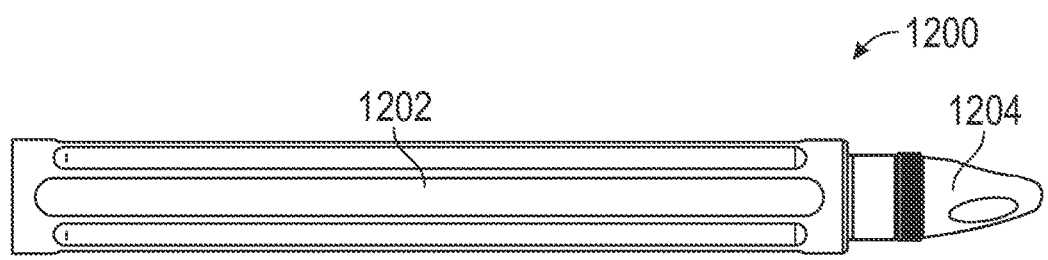
FIG. 12 is a side view of a dart according to another embodiment of the invention.
Figure 13:
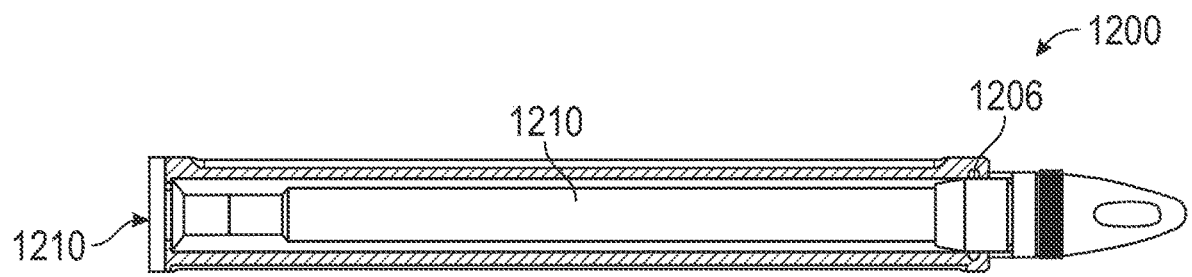
FIG. 13 is a side sectional view of the dart of FIG. 12.

Referring now to FIG. 12, a dart assembly 1200 according to an embodiment of the invention is presented. The dart assembly 1200 comprises a dart 1210 similar to the dart 810 described herein above. The dart assembly further comprises an outer housing 1202 and a proximal cap member 1204. The proximal cap member 1204 may be configured similar to the proximal cap member 806 described above, being removably attachable to a proximal end of the outer housing 1202. The dart assembly 1200 may not include a distal cap member, instead having the distal end of the outer housing 1202 itself comprising an aperture 1203 to facilitate ejection of the dart 1210 from the outer housing 1202. The dart 1210 may abut an inner surface of the distal end of the outer housing 1202 and be held in place by a gasket 1206, in this embodiment at a proximal end of the outer housing 1202.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

What is claimed is:

1. A dart delivery apparatus comprising:
   a handle;
   a trigger;
   a barrel;
   a frame comprising a dart chamber configured to permit a dart assembly to be positioned there within; and
   a pressure control apparatus comprising:
   a gas source port configured to facilitate attachment of a gas source thereto, thereby permitting fluidic communication between the gas source port and the gas source;
   an adjustable pressure control apparatus chamber in fluidic communication with the gas source port;
   a gun port in fluidic communication with the pressure control apparatus chamber and configured to attach to the frame and thereby establish fluidic communication with the dart chamber;
   an expansion chamber positioned in fluidic communication with the gun port;
   an adjustable pressure regulator positioned within the pressure control apparatus chamber configured to be actuated by a user to permit pressurized gas to flow from the gas source port, through the pressure control apparatus chamber, and into the gun port and the expansion chamber, the adjustable pressure regulator comprising:
   a body member defining an internal cavity and configured to establish a fluidic seal with the adjustable pressure control apparatus chamber such that gas may not flow around the body member from a proximal portion of the adjustable pressure control apparatus chamber to a distal portion thereof;
   a translating member positioned within the internal cavity of the body member and comprising a translating member conduit;
   a biasing member configured to bias the translating member in a first position that prevents gas from flowing through the adjustable pressure regulator;
   a distal plug member comprising a distal plug conduit; and
   an actuation member attached to the translating member and configured to be actuated by a user to translate the translating member to a second position that permits gas to flow through from a proximal portion of the adjustable pressure control apparatus chamber though the translating member conduit, the distal portion of the adjustable pressure control apparatus chamber, and the distal plug conduit to the gun port; and a shot volume modification apparatus positioned partially within the expansion chamber and configured to change the volume of the expansion chamber into which pressurized gas may expand.

2. The dart delivery apparatus of claim 1 wherein the frame further comprises:

a loading aperture configured to permit the dart assembly to pass therethrough and be positioned within the dart chamber;

a proximal gasket configured to interface with a proximal section of the dart assembly when the dart assembly is positioned within the dart chamber; and a distal gasket configured to interface with a distal section of the dart assembly when the dart assembly is positioned within the dart chamber.

3. The dart delivery apparatus of claim 1 wherein the frame further comprises:

a gas conduit in fluidic communication with a distal end of the dart chamber;

a gas entry chamber in fluidic communication with the gas conduit;

a trigger valve configured to be actuated by the trigger to permit fluidic flow from the gas entry chamber to the gas conduit; and a gas entry port in fluidic communication with the gas entry chamber and configured to facilitate attachment of the pressure control apparatus thereto.

4. The dart delivery apparatus of claim 1 wherein the pressure control apparatus further comprises a pressure relief apparatus positioned fluidic communication with the gun port and configured to be actuated to permit pressurized gas to flow from the gun port to the environment, thereby de-pressurizing the gun port and the expansion chamber.

5. The dart delivery apparatus of claim 1 wherein the pressure control apparatus further comprises a pressure display positioned and configured to measure a pressure of gas within the gun port and expansion chamber and display the measured pressure.

6. The dart delivery apparatus of claim 1 wherein the shot volume modification apparatus comprises:

an attachment member configured to attach to the expansion chamber and be positioned partially there within;

a cap member attached to a distal end of the attachment member, positioned partially within the expansion chamber and configured to translate longitudinally along the attachment member; and a gasket configured to establish a fluidic seal between the cap member and the expansion chamber such that gas does not flow out of the expansion chamber past the cap member;

wherein the longitudinal translation of the cap member changes the volume of the expansion chamber.

7. A dart delivery apparatus comprising:
a handle;
a trigger;
a barrel;
a frame comprising a dart chamber configured to permit a dart assembly to be positioned there within; and
a pressure control apparatus comprising:

a gas source port configured to facilitate attachment of a gas source thereto, thereby permitting fluidic communication between the gas source port and the gas source;

an adjustable pressure control apparatus chamber in fluidic communication with the gas source port;

a gun port in fluidic communication with the pressure control apparatus chamber and configured to attach to the frame and thereby establish fluidic communication with the dart chamber;

an expansion chamber positioned in fluidic communication with the gun port;

an adjustable pressure regulator positioned within the pressure control apparatus chamber configured to be actuated by a user to permit pressurized gas to flow from the gas source port, through the pressure control apparatus chamber, and into the gun port and the expansion chamber, the adjustable pressure regulator comprising:

a body member defining an internal cavity and configured to establish a fluidic seal with the adjustable pressure control apparatus chamber such that gas may not flow around the body member from a proximal portion of the adjustable pressure control apparatus chamber to a distal portion thereof;

a translating member positioned within the internal cavity of the body member and comprising a translating member conduit;

a biasing member configured to bias the translating member in a first position that prevents gas from flowing through the adjustable pressure regulator;

a distal plug member comprising a distal plug conduit; and an actuation member attached to the translating member and configured to be actuated by a user to translate the translating member to a second position that permits gas to flow through from a proximal portion of the adjustable pressure control apparatus chamber though the translating member conduit, the distal portion of the adjustable pressure control apparatus chamber, and the distal plug conduit to the gun port; and a shot volume modification apparatus positioned partially within the expansion chamber and configured to change the volume of the expansion chamber into which pressurized gas may expand, the shot volume modification apparatus comprising:

an attachment member configured to attach to the expansion chamber and be positioned partially there within;

a cap member attached to a distal end of the attachment member, positioned partially within the expansion chamber and configured to translate longitudinally along the attachment member; and a gasket configured to establish a fluidic seal between the cap member and the expansion chamber such that gas does not flow out of the expansion chamber past the cap member;

wherein the longitudinal translation of the cap member changes the volume of the expansion chamber.

8. The dart delivery apparatus of claim 7 wherein the frame further comprises:

a loading aperture configured to permit the dart assembly to pass therethrough and be positioned within the dart chamber;

a proximal gasket configured to interface with a proximal section of the dart assembly when the dart assembly is positioned within the dart chamber; and a distal gasket configured to interface with a distal section of the dart assembly when the dart assembly is positioned within the dart chamber.

9. The dart delivery apparatus of claim 7 wherein the frame further comprises:
a gas conduit in fluidic communication with a distal end of the dart chamber;
a gas entry chamber in fluidic communication with the gas conduit;
a trigger valve configured to be actuated by the trigger to permit fluidic flow from the gas entry chamber to the gas conduit; and
a gas entry port in fluidic communication with the gas entry chamber and configured to facilitate attachment of the pressure control apparatus thereto.

10. The dart delivery apparatus of claim 7 wherein the pressure control apparatus further comprises a pressure relief apparatus positioned fluidic communication with the gun port and configured to be actuated to permit pressurized gas to flow from the gun port to the environment, thereby de-pressurizing the gun port and the expansion chamber.

11. The dart delivery apparatus of claim 7 wherein the pressure control apparatus further comprises a pressure display positioned and configured to measure a pressure of gas within the gun port and expansion chamber and display the measured pressure.

12. A dart delivery apparatus comprising:
a handle;
a trigger;
a barrel;
a frame comprising:
  a dart chamber configured to permit a dart assembly to be positioned there within;
  a loading aperture configured to permit a dart assembly to pass therethrough and be positioned within the dart chamber;
  a proximal gasket configured to interface with a proximal section of a dart assembly when the dart assembly is positioned within the dart chamber;
  a distal gasket configured to interface with a distal section of a dart assembly when the dart assembly is positioned within the dart chamber;
  a gas conduit in fluidic communication with a distal end of the dart chamber;
  a gas entry chamber in fluidic communication with the gas conduit;
  a trigger valve configured to be actuated by the trigger to permit fluidic flow from the gas entry chamber to the gas conduit;
  a gas entry port in fluidic communication with the gas entry chamber; and
a pressure control apparatus comprising:
  a gas source port configured to facilitate attachment of a gas source thereto, thereby permitting fluidic communication between the gas source port and the gas source;
  an adjustable pressure control apparatus chamber in fluidic communication with the gas source port;
  a gun port in fluidic communication with the pressure control apparatus chamber and configured to attach to the gas entry port of the frame;
  an expansion chamber positioned in fluidic communication with the gun port;
  an adjustable pressure regulator positioned within the pressure control apparatus chamber configured to be actuated by a user to permit pressurized gas to flow from the gas source port, through the pressure control apparatus chamber, and into the gun port and the expansion chamber, the adjustable pressure regulator comprising:
    a body member defining an internal cavity and configured to establish a fluidic seal with the adjustable pressure control apparatus chamber such that gas may not flow around the body member from a proximal portion of the adjustable pressure control apparatus chamber to a distal portion thereof;
    a translating member positioned within the internal cavity of the body member and comprising a translating member conduit;
    a biasing member configured to bias the translating member in a first position that prevents gas from flowing through the adjustable pressure regulator;
    a distal plug member comprising a distal plug conduit; and
    an actuation member attached to the translating member and configured to be actuated by a user to translate the translating member to a second position that permits gas to flow through from a proximal portion of the adjustable pressure control apparatus chamber though the translating member conduit, the distal portion of the adjustable pressure control apparatus chamber, and the distal plug conduit to the gun port;
  a shot volume modification apparatus positioned partially within the expansion chamber and configured to change the volume of the expansion chamber into which pressurized gas may expand;
  a pressure display positioned and configured to measure a pressure of gas within the gun port and expansion chamber and display the measured pressure; and
  a pressure relief apparatus positioned fluidic communication with the gun port and configured to be actuated to permit pressurized gas to flow from the gun port to the environment, thereby de-pressurizing the gun port and the expansion chamber.

13. The dart delivery apparatus of claim 12 wherein the frame further comprises:
a loading aperture configured to permit a dart assembly to pass therethrough and be positioned within the dart chamber;
a proximal gasket configured to interface with a proximal section of the dart assembly when the dart assembly is positioned within the dart chamber; and
a distal gasket configured to interface with a distal section of the dart assembly when the dart assembly is positioned within the dart chamber.

14. The dart delivery apparatus of claim 12 wherein the frame further comprises:
a gas conduit in fluidic communication with a distal end of the dart chamber;
a gas entry chamber in fluidic communication with the gas conduit;
a trigger valve configured to be actuated by the trigger to permit fluidic flow from the gas entry chamber to the gas conduit; and
a gas entry port in fluidic communication with the gas entry chamber and configured to facilitate attachment of the pressure control apparatus thereto.

15. The dart delivery apparatus of claim 12 wherein the pressure control apparatus further comprises a pressure display positioned and configured to measure a pressure of gas within the gun port and expansion chamber and display the measured pressure.

16. The dart delivery apparatus of claim 12 wherein the shot volume modification apparatus comprises:
- an attachment member configured to attach to the expansion chamber and be positioned partially there within;
- a cap member attached to a distal end of the attachment member, positioned partially within the expansion chamber and configured to translate longitudinally along the attachment member; and
- a gasket configured to establish a fluidic seal between the cap member and the expansion chamber such that gas does not flow out of the expansion chamber past the cap member;
- wherein the longitudinal translation of the cap member changes the volume of the expansion chamber.

* * * * *